United States Patent [19]

Natori et al.

[11] Patent Number: 6,111,152

[45] Date of Patent: Aug. 29, 2000

[54] METHOD FOR SEPARATING VINYL CHLORIDE FROM A THERMALLY DECOMPOSED PRODUCT OF 1,2-DICHLOROETHANE

[75] Inventors: Yukikazu Natori, Kanagawa; Shinji Yamamoto; Kazutoshi Itoyama, both of Okayama; Tetsuhiro Yamauchi, Ibaraki, all of Japan

[73] Assignee: Mitsubishi Chemical Corporation, Tokyo, Japan

[21] Appl. No.: 09/312,963

[22] Filed: May 17, 1999

[30] Foreign Application Priority Data

May 18, 1998 [JP] Japan .................................. 10-134765

[51] Int. Cl.⁷ ............................. C07C 17/25; C07C 17/38
[52] U.S. Cl. ............................................ 570/226; 570/238
[58] Field of Search ...................................... 570/226, 238

[56] References Cited

U.S. PATENT DOCUMENTS 4,822,932   4/1989   Dummer et al. ........................ 570/226

*Primary Examiner*—Deborah D. Carr
*Assistant Examiner*—J. Parsa
*Attorney, Agent, or Firm*—Oblon, Spivak, McClelland, Maier & Neustadt, P.C.

[57] ABSTRACT

A method for separating vinyl chloride, which comprises cooling a cracked gas obtained by cracking 1,2-dichloroethane by a thermal cracking furnace, firstly in a heat exchanger, then further cooling it in a quenching tower and then distilling it, wherein the cracked gas is cooled in the heat exchanger to at least 350° C., the quenching tower is controlled so that from 80 to 98 wt % of the cracked gas introduced is withdrawn as an overhead product and the rest of from 20 to 2 wt % of the cracked gas is withdrawn as a bottom effluent, and they are respectively sent to the subsequent steps, and formed coke is discharged together with the bottom effluent.

6 Claims, 2 Drawing Sheets

METHOD FOR SEPARATING VINYL CHLORIDE FROM A THERMALLY DECOMPOSED PRODUCT OF 1,2-DICHLOROETHANE

BACKGROUND OF THE INVENTION

1. Field of the Invention

The present invention relates to a method for separating vinyl chloride (hereinafter referred to simply as VCM) via cooling and a purification step such as distillation, from a gas formed by thermal cracking of 1,2-dichloroethane (hereinafter referred to simply as EDC). Particularly, the present invention relates to a method wherein the gas formed by thermal cracking of EDC is cooled in specific steps, and formed coke is efficiently separated to prevent a trouble in the subsequent step for separating VCM.

2. Discussion of Background

Heretofore, as a method for producing VCM, a method is known wherein EDC is thermally cracked at a temperature of from 450 to 550° C. in a thermal cracking furnace, and the formed cracked gas is cooled and then VCM is separated by distillation. The high temperature cracked gas discharged from the cracking furnace contains VCM and hydrogen chloride as cracked products, and noncracked EDC mainly, and it is supplied to a quenching tower as it is, or it is indirectly cooled by a heat exchanger and then supplied to a quenching tower, where the heat of the high temperature cracked gas is recovered.

In such a method, it is known that coke will deposit in the cooling pipe of the heat exchanger used for cooling the cracked gas to cause deterioration of the performance, increase of the pressure loss and clogging of the pipe, and it is impossible to conduct a continuous operation over a long period of time.

Therefore, JP-B-6-92328 proposes to carry out heat exchange of EDC to be supplied to the thermal cracking furnace with a high temperature cracked gas discharged from the cracking furnace by permitting the cracked effluent gas to flow through a pipe at a flow rate of at least 5 m/sec and less than 20 m/sec and cooling the cracked effluent gas to a temperature of from 180 to 350° C., whereby it is said to be possible to prolong the continuous operation period of the thermal cracking furnace. However, in this method, the cracked gas cooled in a heat exchanger is introduced as it is to the conventional quenching tower, then quenched to e.g. 80° C. and then sent to the subsequent step, whereby the bottom liquid is withdrawn in a large amount, and it is difficult to sufficiently separate coke from the bottom liquid before supplying the bottom liquid to a hydrogen chloride tower. Further, JP-A-6-219977 discloses a method in which a specific cooler which is single pipe of from 150 to 250 mm and which employs the bottom liquid of an EDC distillation tower as a cooling medium, is used for indirectly cooling the cracked gas, and the cracked gas is permitted to flow in the single pipe of the cooler under a pressure of from 0.9 to 1.4 MPa and cooled at an average cooling rate of from 15 to 45° C./sec until the cracked gas temperature at the outlet of the cooler becomes from 250 to 350° C., and EDC thermally recovered by a cooling medium in the cooler is directly refluxed to the EDC distillation tower, whereby the cracked gas withdrawn from the cooler is quenched to a level of from 40 to 150° C. in a quenching tower, and VCM is recovered in the subsequent step, but the bottom effluent withdrawn from the bottom of the quenching tower is separately treated without passing through a distillation purification step.

This method has a merit such that the continuous operation periods of the thermal cracking furnace and the cooler can be prolonged equally to sixth months. However, the effluent from the bottom of the quenching tower is separately treated, thus leading to a disadvantage such as a loss of EDC or VCM in the effluent.

SUMMARY OF THE INVENTION

In the production of VCM by thermal cracking of EDC, formation of coke in the step of cooling the cracked gas brings about a serious hindrance to maintain continuous operation. Accordingly, it has been attempted to avoid such formation of coke, but such attempts have been mainly for the purpose of suppressing the formation by changing the operation conditions of the thermal cracking furnace. However, it is difficult to completely suppress formation of coke, and it is desired to efficiently treat formed coke to avoid a trouble against the continuous operation.

The present inventors have conducted an extensive study on the mechanism for the formation of coke in each step from cooling of the cracked gas of EDC to separation of VCM and as a result, have found that the nature of formed coke differs depending upon the temperature for treatment of the cracked gas, and the handling efficiency of coke differs depending upon the nature. It has also been found that coke formed under certain specific conditions can be removed by an extremely simple separation operation, and as a result, constant operation for a long period of time can be made possible. The present invention has been accomplished on the basis of these discoveries.

The present invention is directed to a method for separating VCM which comprises cooling a cracked gas discharged from a thermal cracking furnace of EDC by indirect cooling to a predetermined temperature, and then cooling it in a quenching tower, wherein the conditions for indirect cooling and operation of the quenching tower, are controlled, so that coke is efficiently separated thereby to prevent a trouble in the subsequent distillation step.

Namely, the present invention provides a method for separating vinyl chloride, which comprises cooling a cracked gas obtained by cracking 1,2-dichloroethane by a thermal cracking furnace, firstly in a heat exchanger, then further cooling it in a quenching tower and then distilling it, wherein the cracked gas is cooled in the heat exchanger to at least 350° C., the quenching tower is controlled so that from 80 to 98 wt % of the cracked gas introduced is withdrawn as an overhead product and the rest of from 20 to 2 wt % of the cracked gas is withdrawn as a bottom effluent, and they are respectively sent to the subsequent steps, and formed coke is discharged together with the bottom effluent.

DETAILED DESCRIPTION OF THE PREFERRED EMBODIMENTS

Figure 1:
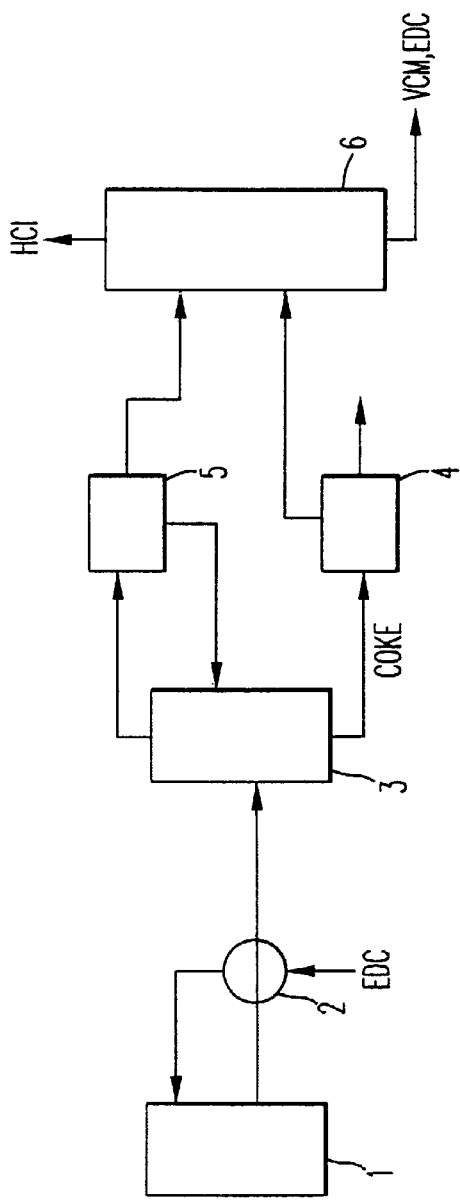
FIG. 1 is a flow sheet of the apparatus used in the method of the present invention.

Now, the present invention will be described in detail.

When VCM is produced by thermal cracking of EDC, coke will form, but the nature of the coke depends on the formation temperature, and cokes may be classified into hard coke having a high density and soft coke having a low density. In a case where a high temperature cracking furnace gas is once cooled to a predetermined temperature by indirect cooling and then cooled again, hard coke will mainly form, and at a place where the high temperature cracked gas is quenched, soft coke will mainly form.

If the cracked gas of from 450 to 550° C. discharged from the thermal cracking furnace is quenched directly in a quenching tower as in a conventional method, soft coke will be formed in a large amount, and formed soft coke has a low density and is accordingly discharged from the tower top and brings about fouling or erosion of the subsequent pipelines or instruments, thus leading to clogging of a heat exchanger, clogging of trays or packing materials in a hydrogen chloride tower, fouling or clogging of reboiler tubes, thus creating a trouble in operation and making constant operation for a long period of time impossible. By reducing the amount of the gas discharged from the tower top, it is possible to suppress discharge or scattering of soft coke from the tower top, but the heat recovery from the gas discharged from the tower top will decrease, and at the same time, a coke separation apparatus of a large size will be required for the tower bottom, which are economically disadvantageous. Accordingly, by the method of introducing a high temperature cracked gas directly to a quenching tower for quenching, it is difficult to prolong the operation time, since soft coke will form in the quenching tower.

In the present invention, without directly cooling the high temperature cracked gas from a thermal cracking furnace in a quenching tower, the cracked gas is cooled firstly in a heat exchanger to a predetermined temperature and then cooled in a quenching tower. In this manner, the cracked gas is cooled to a temperature around the temperature for formation of tar-like coke, before being supplied to the quenching tower, whereby coke to be formed in the tower, will be hard coke having a high density. The hard coke can be discharged from the tower bottom together with the bottom effluent, whereby constant long term operation has been made possible by avoiding fouling troubles of the subsequent equipments due to discharge of soft coke from the tower top. Besides, the hard coke in the bottom effluent can easily be separated and removed by a mechanical means such as filtration, and the effluent after separation of coke, can be supplied to the hydrogen chloride tower in the next step and can be treated together with the overhead product. Thus, the method is advantageous without a loss of EDC or VCM.

Now, the practical embodiment of the method of the present invention will be described with reference to FIG. 1. The thermal cracking in the thermal cracking furnace (1) of EDC in the present invention, is carried out by a conventional method by introducing liquid or gasified EDC into the thermal cracking furnace. The thermal cracking is carried out usually at a temperature of from 450 to 550° C., and the temperature of the cracked gas discharged from the thermal cracking furnace is also at a level of from 450 to 550° C. In the cracked gas, non-cracked EDC and byproducts such as methyl chloride, benzene and chloroprene, are contained in addition to VCM and hydrogen chloride as the main products.

The cracked gas of from 450 to 550° C. discharged from the thermal cracking furnace is firstly sent to a heat exchanger (2) for heat recovery and indirectly cooled.

In the present invention, this cracked gas is required to be cooled to at least 350° C. in the heat exchanger, and it is cooled preferably to 200° C., more preferably to a level within a range of from 300 to 200° C. If the cooled temperature is higher than this temperature level, the heat recovery tends to be small, such being uneconomical, and not only that, the gas discharged from the heat exchanger will be excessively quenched in the subsequent quenching tower, whereby soft coke is likely to be formed in the quenching tower and will adversely affect the subsequent operation for separation. On the other hand, if it is cooled too much, there will be a trouble such as formation of coke or clogging of a pipe, in the heat exchanger.

The shape of the heat exchanger to be used for indirect cooling is not particularly limited, and a single pipe or multi pipe heat exchanger may be used. As a cooling medium to cool the cracked gas supplied to the heat exchanger, any medium may be employed so long as it is capable of effectively recovering the heat of the high temperature cracked gas to utilize it as another heat source and cooling the cracked gas to the desired temperature, and it is not limited to a commonly employed heat medium, boiler water or EDC. However, it is advantageous to use EDC as a cooling medium, since EDC gasified in the heat exchanger can be supplied as a material to the thermal cracking furnace, whereby it will be possible to establish an energy saving self-sustaining system. The flow rate, supply pressure, etc. of the cracked gas supplied to the heat exchanger, are optionally determined, taking into consideration the type of the heat exchanger, the cooled temperature, and operational conditions of the thermal cracking furnace or subsequent quenching tower (3), etc.

The cracked gas cooled to the predetermined temperature, which is discharged from the heat exchanger, will be supplied to a quenching tower (3) and cooled. In the present invention, it is important that the divided flow ratio (wt %) of the overhead product to the bottom effluent, to be withdrawn from the quenching tower and sent to the subsequent step, is controlled to be 80 to 98:20 to 2, preferably 90 to 98:10 to 2, and formed coke is discharged together with the bottom effluent.

To control the divided flow ratio of the quenching tower to be within such a proportion, the bottom temperature of the quenching tower is usually from 140 to 190° C., and the tower top pressure of the quenching tower is from 12 to 21 kg/cm$^2$G, preferably the bottom temperature is from 155 to 180° C., and the tower top pressure is from 16 to 20 kg/cm$^2$G. Thus, the bottom temperature is high as compared with the conventional methods. By the cooling by means of the heat exchanger, coke formed in the quenching tower, becomes hard coke having a high density, and most of the formed coke can be discharged from the tower bottom together with the bottom effluent.

If the cracked gas is indirectly cooled by a heat exchanger and then cooled in a quenching tower under the same conditions as in the conventional method, a certain effect may be observed from the viewpoint that the operation period of the cracking furnace can be prolonged, but soft coke will form in the quenching tower, whereby a trouble of fouling with coke of the subsequent instruments, can not be avoided. Namely, by adjusting the operation conditions in the heat exchanger and in the quenching tower to the conditions defined in the present invention, it is possible for the first time to obtain excellent effects which make constant long term operation possible.

This bottom effluent contains non-cracked EDC and a part of VCM, and further coke and high boiling substances. This effluent is subjected to removal of hard coke by a separating apparatus (4) and then supplied to the subsequent hydrogen chloride tower (6), wherein it is distilled together with the overhead product and separated from hydrogen chloride (HCl). The separating apparatus may be any apparatus so long as it is capable of separating hard coke, and usually, a filtration apparatus or a flush drum or the like, is used. The separated coke may be subjected to treatment to recover EDC, etc. accompanying the coke, as the case requires.

The gas discharged from the tower top is a mixture comprising mainly hydrogen chloride, VCM and non-cracked EDC. This discharged gas is cooled and separated in a separation/cooling apparatus (5), whereupon a part will be recycled to the quenching tower and countercurrently contacted with the cracked gas to contribute to cooling in the quenching tower, and the rest will be supplied to the hydrogen chloride tower. In the hydrogen chloride tower, hydrogen chloride is discharged from the tower top, and an effluent containing mainly EDC and VCM is obtained from the tower bottom. This effluent is rectified in accordance with a conventional method to recover VCM.

In the method of the present invention, the cracked gas is cooled by indirect cooling by means of the heat exchanger (2) to a predetermined temperature and then cooled in the quenching tower under the predetermined conditions, so that hard coke is selectively formed. This formed coke is withdrawn together with the bottom effluent from the quenching tower, and yet the bottom effluent is in a small amount. Therefore, it will be possible to reduce the size of the coke treatment installation, and further, by the provision of the heat exchanger (2), it is also possible to reduce the tower diameter of the quenching tower. Thus, installation costs can be reduced, and the method of the present invention is an economically advantageous method.

Now, the method of the present invention will be described in further detail with reference to Examples and Comparative Examples. However, it should be understood that the present invention is by no means restricted to such specific Examples.

EXAMPLE 1

By the apparatus as shown in FIG. 1, thermal cracking of EDC was carried out to produce VCM.

Gaseous EDC preliminarily heated to 230° C., was supplied to the thermal cracking furnace (1) at a flow rate of 107.86 parts/hr. The cracking temperature of the cracking furnace was 490° C., and the cracking pressure was 19/cm²G, whereby about 53% of supplied EDC was cracked.

The cracked gas (490° C.) discharged from the thermal cracking furnace was introduced to the heat exchanger (2). The heat exchanger was a single pipe vertical type, and as a cooling liquid medium, EDC (220° C.) was supplied. The temperature of the cracked gas discharged from the outlet of the heat exchanger was 300° C. The cooled cracked gas was supplied to the quenching tower (3), and the quenching tower was operated at a tower bottom temperature of 167.9° C., at a tower top temperature of 165.8° C. under a tower top pressure of 18.5 kg/cm²G, whereby from the tower bottom, the bottom effluent was withdrawn at a rate of 5.35 parts/hr, and the rest was withdrawn from the tower top as the overhead product. Here, the weight ratio of the overhead product to the bottom effluent was 95.0:5.0.

In the effluent from the tower bottom, coke was contained in addition to VCM, EDC, high boiling substances, etc. Therefore, after removing coke by the separating apparatus (4), the effluent was sent to the hydrogen chloride tower and treated together with the overhead product. On the other hand, the overhead product was supplied to the hydrogen chloride tower, and by distillation, HCl was distilled and recovered from the tower top, and the tower bottom liquid was rectified by a VCM tower (not shown) to recover VCM. EDC gasified by the heat exchanger was supplied as starting material EDC to the thermal cracking furnace.

Under these conditions, continuous operation was carried out, and each of the cracking furnace, the quenching tower and the hydrogen chloride tower was operated at least 11 months, and thus it was possible to prolong the operation period substantially. Further, scatter of coke was not observed, and no cleaning operation of equipments was required.

EXAMPLE 2

In the apparatus as shown in FIG. 1, boiler water (pure water) was employed instead of EDC, as a cooling liquid medium for the heat exchanger (2). The thermal cracking was carried out under the same conditions as in Example 1, except that gaseous EDC was supplied at a flow rate of 116.64 parts/hr.

The cracked gas (490° C.) discharged from the thermal cracking furnace was introduced into the heat exchanger (2). The temperature of the cracked gas discharged from the outlet of the heat exchanger was 280° C. The cooled cracked gas was supplied to the quenching tower (3). The quenching tower was operated at a tower bottom temperature of 165.4° C., at a tower top temperature of 157.5° C. under a tower top pressure of 16.85 kg/cm²G, whereby an overhead product was withdrawn at a rate of 110.69 parts/hr from the tower top, and a bottom effluent was withdrawn at a flow rate of 5.95 parts/hr from the tower bottom. Here, the weight ratio of the overhead product to the bottom effluent was 94.9:5.1.

The respective effluents withdrawn from the quenching tower were treated in the same manner as in Example 1. By the operation under the above-described conditions, it was possible to continuously operate each of the cracking furnace, the quenching tower and the hydrogen chloride tower constantly for at least 11 months. Further, scatter of coke was not observed, and no cleaning operation of equipments was required.

Comparative Example 1

Figure 2:
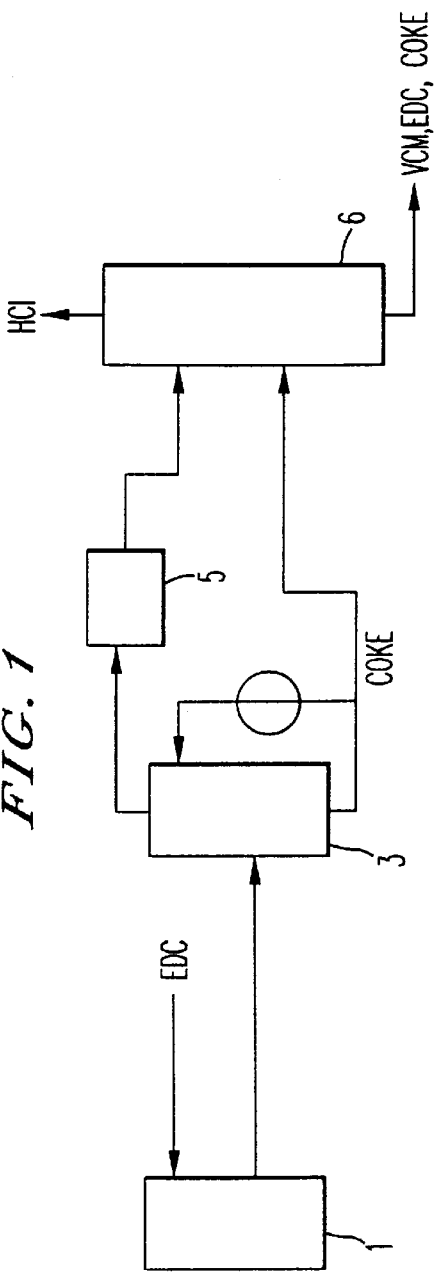
FIG. 2 is a flow sheet of apparatus used in the method of Comparative Example 1.

By the apparatus shown in FIG. 2, thermal cracking of EDC was carried out to produce VCM. Liquid EDC preliminarily heated to 205° C., was supplied to the thermal cracking furnace (1) at a flow rate of 96.5 parts/hr. The cracking temperature of the cracking furnace was 510° C., the cracking pressure was 32 kg/cm²G, and the operation was carried out at a cracking rate of supplied EDC of about 52%.

The cracked gas (510° C.) discharged from the thermal cracking furnace was supplied directly to the quenching tower (3) and quenched. The quenching tower was operated at a tower bottom temperature of 89° C., at a tower top temperature of 85° C. under a tower top pressure of 18 kg/cm²G, whereby the overhead product was withdrawn at a flow rate of 41.8 parts/hr from the tower top, and the bottom effluent was withdrawn at a flow rate of 54.7 parts/hr from the tower bottom. Here, the weight ratio of the overhead product to the bottom effluent was 43.3:56.7.

Under these conditions, continuous operation was carried out. As a result, the performance of the cooler for the tower bottom liquid of the quenching tower decreased by coke, and cleaning operations were required at a frequency of about once a month. Further, soft coke discharged together with the overhead product was transported to the hydrogen chloride tower and fouled the equipments.

Comparative Example 2

Figure 3:
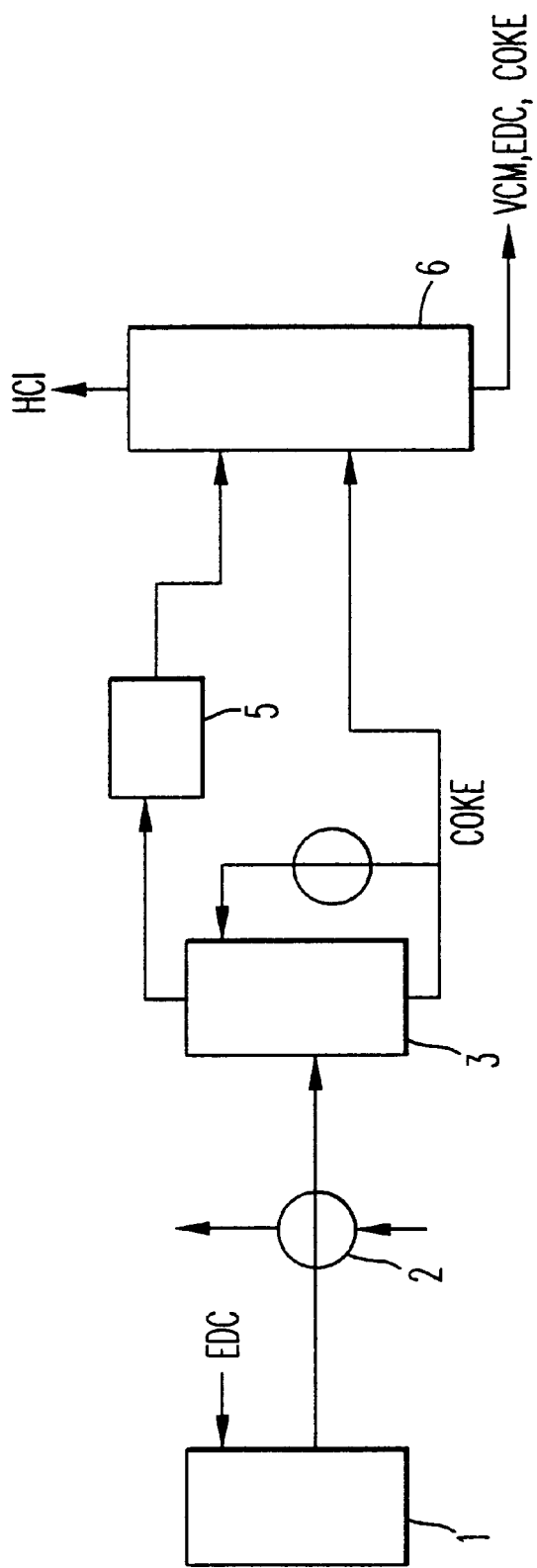
FIG. 3 is a flow sheet of apparatus used in the method of Comparative Example 2.

By the apparatus shown in FIG. 3, thermal cracking of EDC was carried out to produce VCM. Gaseous EDC preliminarily heated to 230° C., was supplied to the thermal cracking furnace (1) at a flow rate of 96.5 parts/hr. The cracking temperature of the cracking furnace was 487° C., the cracking pressure was 18.5 kg/cm$^2$G, and the operation was carried out at a cracking rate of supplied EDC of about 52%.

The cracked gas (487° C.) discharged from the thermal cracking furnace was introduced into the heat exchanger (2). To the heat exchanger, EDC (220° C.) was supplied as a cooling liquid medium. The temperature of the cracked gas discharged from the outlet of the heat exchanger was 200° C. The cooled cracked gas was supplied to the quenching tower (3) and cooled. The quenching tower was operated at a tower bottom temperature of 89° C., at a tower top temperature of 85° C. under a tower top pressure of 18 kg/cm$^2$G, whereby the overhead product was withdrawn at a flow rate of 41.8 parts/hr from the tower top, and the bottom effluent was withdrawn at a flow rate of 54.7 parts/hr from the tower bottom. Here, the weight ratio of the overhead product to the bottom effluent was 43.3:56.7.

Under these conditions, continuous operation was carried out, and as a result, the efficiency of the cooler for the tower bottom liquid of the quenching tower decreased by coke, and cleaning operations were required at a frequency of once per 6 months.

Comparative Example 3

By the same apparatus as in FIG. 1 except that no heat exchanger (2) for indirect cooling of the cracked gas is provided, thermal cracking of EDC was carried out to produce VCM.

Liquid EDC preliminarily heated to 143° C. was supplied to the thermal cracking furnace (1) at a flow rate of 94.4 parts/hr. The cracking temperature of the cracking furnace was 498° C., the cracking pressure was 26.4 kg/cm$^2$G, and the operation was carried out at a cracking rate of supplied EDC of about 52%.

The cracked gas (498° C.) discharged from the thermal decomposition furnace was supplied directly to the quenching tower (3) and quenched. The quenching tower was operated at a tower bottom temperature of 192.1° C., at a tower top temperature of 185.6° C., under the tower top pressure of 21.8 kg/cm$^2$G, whereby the overhead product was withdrawn at a flow rate of 90.37 parts/hr from the tower top, and the bottom effluent was withdrawn at a flow rate of 4.03 parts/hr from the tower bottom. Here, the weight ratio of the overhead product to the bottom effluent was 95.7:4.3.

The bottom effluent and the overhead product were treated in the same manner as in Example 1.

Under these conditions, continuous operation was carried out, whereby the quenching tower and equipments coke, and cleaning operations were required at a frequency of once per 3 months.

As described in the foregoing, according to the method of the present invention, the crack ed gas of EDC is cooled by indirect cooling to a predetermined temperature and then cooled in a quenching tower under the predetermined conditions, whereby hard coke is selectively formed, and formed coke is withdrawn together with the bottom effluent from the quenching tower, whereby it is possible to prevent fouling by coke of the quenching tower and the subsequent equipments and to carry out the operation constantly for a long period of time. Further, the bottom effluent from the quenching tower is in a small amount, whereby reduction of the installation becomes possible. Thus, the method of the present invention is economically advantageous.

What is claimed is:

1. A method for separating vinyl chloride, which comprises cooling a cracked gas obtained by cracking 1,2-dichloroethane by a thermal cracking furnace, firstly in a heat exchanger, then further cooling it in a quenching tower and then distilling it, wherein the cracked gas is cooled in the heat exchanger to at least 350° C., the quenching tower is controlled so that from 80 to 98 wt % of the cracked gas introduced is withdrawn as an overhead product and the rest of from 20 to 2 wt % of the cracked gas is withdrawn as a bottom effluent, and they are respectively sent to the subsequent steps, and formed coke is discharged together with the bottom effluent.

2. The separation method according to claim 1, wherein the bottom effluent containing the coke discharged from the quenching tower is subjected to distillation after separating the coke.

3. The separation method according to claim 1, wherein the cracked gas is cooled in the heat exchanger to a level of from 200 to 350° C.

4. The separation method according to claim 1, wherein liquid 1,2-dichloroethane is used as a cooling medium for the heat exchanger, and 1,2-dichloroethane vaporized in the heat exchanger is introduced into the thermal cracking furnace.

5. The separation method according to claim 1, wherein the bottom temperature of the quenching tower is controlled within a range of from 140 to 190° C., and the pressure in the quenching tower is controlled within a range of from 12 to 21 kg/cm$^2$G.

6. The separation method according to claim 1, wherein the bottom temperature of the quenching tower is controlled within a range of from 155 to 180° C., and the pressure of the quenching tower is controlled within a range of from 16 to 20 kg/cm$^2$G.

* * * * *